United States Patent [19]

Feiertag et al.

[11] 4,381,666
[45] May 3, 1983

[54] METHOD FOR THE NONDESTRUCTIVE TESTING OF CELLULAR METALLICS

[75] Inventors: Frederick J. Feiertag, Seattle; Dale L. McLellan, Bellevue, both of Wash.

[73] Assignee: The Boeing Company, Seattle, Wash.

[21] Appl. No.: 257,679

[22] Filed: Apr. 27, 1981

[51] Int. Cl.³ ............................................. G01N 33/20
[52] U.S. Cl. ........................................................ 73/87
[58] Field of Search ...................... 73/87, 104, 432 PS

[56] References Cited

U.S. PATENT DOCUMENTS

| | | | |
|---|---|---|---|
| 3,086,391 | 4/1963 | Thomas et al. | 73/87 |
| 3,496,766 | 2/1970 | Stein . | |
| 3,586,546 | 6/1971 | Averbach et al. | 148/128 |
| 3,940,976 | 3/1976 | Fastner | 73/104 |
| 4,063,644 | 12/1977 | Hoffman et al. | 209/111.6 |

OTHER PUBLICATIONS

Spear, R. E. et al. *Dendrite Cell Size, from Transactions of American Foundrymens Society*, 1963, pp. 209–215.
Serra, A. J. et al. *Covariograns for Dendrite Arm Spacing Measurements from Transactions of Metallurgical Society* of AIME, vol. 245, Jan. '69, pp. 55–59.
Bossing, E. N. et al. *Advances in Foundry Quality Control Practices from Metal Progress* Oct. 1974, pp. 115–117.
Frederick, S. F. et al. *The Relation of Ductility . . . Alloy from Transactions of Metallurgical Society* of AIME vol. 242, Oct. '68, pp. 2063–2067.
Leitz-T.A.S. *Texture Analysing System* Brochure by Ernst Leitz Wetzlar GmbH West Germany, Jul. 1978.

*Primary Examiner*—Jerry W. Myracle
*Attorney, Agent, or Firm*—William C. Anderson

[57] ABSTRACT

Method of nondestructively measuring percent elongation or ductility of a cellular metallic. After surface preparation, the number of metal cells per unit area are counted, either manually or using an automated technique. The cell count is utilized in a relationship unique to the cellular metallic which correlates cell count to ductility in terms of percent elongation. The effects of the structural configuration of the cellular metallic, porosity and eutectic morphology are also discussed.

9 Claims, 9 Drawing Figures

METHOD FOR THE NONDESTRUCTIVE TESTING OF CELLULAR METALLICS

TECHNICAL FIELD

This invention relates to a method of testing the mechanical strength characteristics of metals. More particularly, the present invention relates to a method of nondestructively ascertaining the average ductility of a cellular metallic.

BACKGROUND OF THE INVENTION

The delivery of products of consistent dimensions, properties and capabilities, etc., necessitates quality control methodology. No special problems exist in obtaining homogenous and uniform products on a batch or continuous production basis for certain products (e.g., wrought products). Such products allow proper statistical sampling and testing whereby acceptable representative product quality information may be derived.

Other products vary greatly in quality precluding random or scheduled sampling from a number of these products. Under these conditions even apparently parallel production conditions will not give insurances that a selected product will meet the necessary specifications for its intended service. Testing of each product is therefore generally the only method of predicting that the selected product or sample is qualified for its intended use. Obviously, however, such testing is only viable if the sample is not damaged or destroyed by the testing.

For example, castings made of metals such as aluminum, present serious quality control problems since the castings produced within a production run of the same or a different manufacturer vary substantially in physical properties. Tensile properties, e.g., may vary between casting zones in the same casting due to, e.g., differences in local rates of solidification. Natural variations may also occur between castings due to slight changes within the acceptable limits for adding of the constituents to form the alloy and the latitudes of time and temperature of heat treatment processing.

The present state of the casting art, especially the aluminum casting art, is not capable of economically mass producing castings of statistically controllable or predictable properties. Furthermore, the tests from which a skilled artesan can usually select for determining mechanical properties such as percent elongation or ductility, yield strength, tensile strength, weaken or destroy the casting.

Recently, mechanical properties of castings have been ascertained by nondestructive procedures wherein test bars poured from the same metal and at the same time as the actual casting are destructively tested and by means of coupon test bars which are poured as an integral part of the casting and broken off at the time of completion of any heat treatment of the cast article. In the latter procedure the coupon test bars are also destructively tested. However, both the former and the latter procedure, exemplified by U.S. Pat. No. 3,496,766 issued Feb. 24, 1970 to Stein, provide a mere differential determination of the structural properties of the casting. Both methods are therefore incapable of providing reliable information on the properties of the metal in a particular zone which may have responded to heat treatment differently from another zone.

Other conventional non-destructive methods have attempted to use microstructural parameters such as dendrite arm spacing, dendrite cell size and dendrite cell interval to estimate the strength and the ductility of metals. However, such testing methods are difficult to use and produce unreliable results. These secondary arm linear parameters seem to be most indicative of solidification rates and grain refinement. However, these dendrite measurements are extremely difficult to make due to the improbability of obtaining the exact metallurgical mount surface orientation needed to view their true dimensions.

SUMMARY OF THE INVENTION

It is an object of the present invention to provide a nondestructive method for ascertaining the ductility of a cellular metallic as measured by percent elongation.

Another object of the invention is to provide a method for rapidly, accurately and reliably determining the ductility of a volume of a zone of a cellular metallic sample in any arbitrary stress zone.

A further object is to provide a method of nondestructively determining the acceptability of a selected cellular metallic sample to assure quality in mass production.

The present invention is based on the discovery of a unique relationship which correlates a microstructural parameter of a cellular metallic sample to ductility. More specifically, the instant invention provides a method of correlating the number of metal cells in a unit surface area of a zone to the percent tensile elongation of the cellular metallic sample in that zone. After surface preparation of the selected area of the cellular metallic sample, a manual or an automated image analysis technique may be used to count the cells which contribute significantly to ductility within the zone. An empirically derived relationship may then be used to obtain the ductility (as measured by percent elongation) for the selected zone.

DESCRIPTION OF THE PREFERRED EMBODIMENT

The present invention will be described with respect to a cellular metallic which has been cast. In particular, the present invention will be described in reference to a casting of an aluminum based alloy known in the trade as A357 per military specification MIL-A-21180C. This well-known alloy comprises mainly aluminum, silicon and magnesium. However, the present invention is believed applicable to any cellular metallic which has been processed by any method.

The mechanical properties of any selected volume of a given casting are dependent upon the chemical composition of the selected cellular metallic, heat treatment, solidification rates and integrity of the cast structure. Metallurgically in the present case, formation of the aluminum cellular structure controls the basic ductility potential. Specifically, it has been found that ductility of the volume of a selected zone of a cellular metallic can be nondestructively measured by counting the number of metal cells in a surface area of that zone. An empirical relationship, unique to the cellular metallic selected, has been developed which correlates the metal cell count to the percent elongation or ductility within that zone of the cellular metallic. Of course, the ductility measurement can also be related to other zonal strength characteristics of the cellular metallic.

Figure 1A:
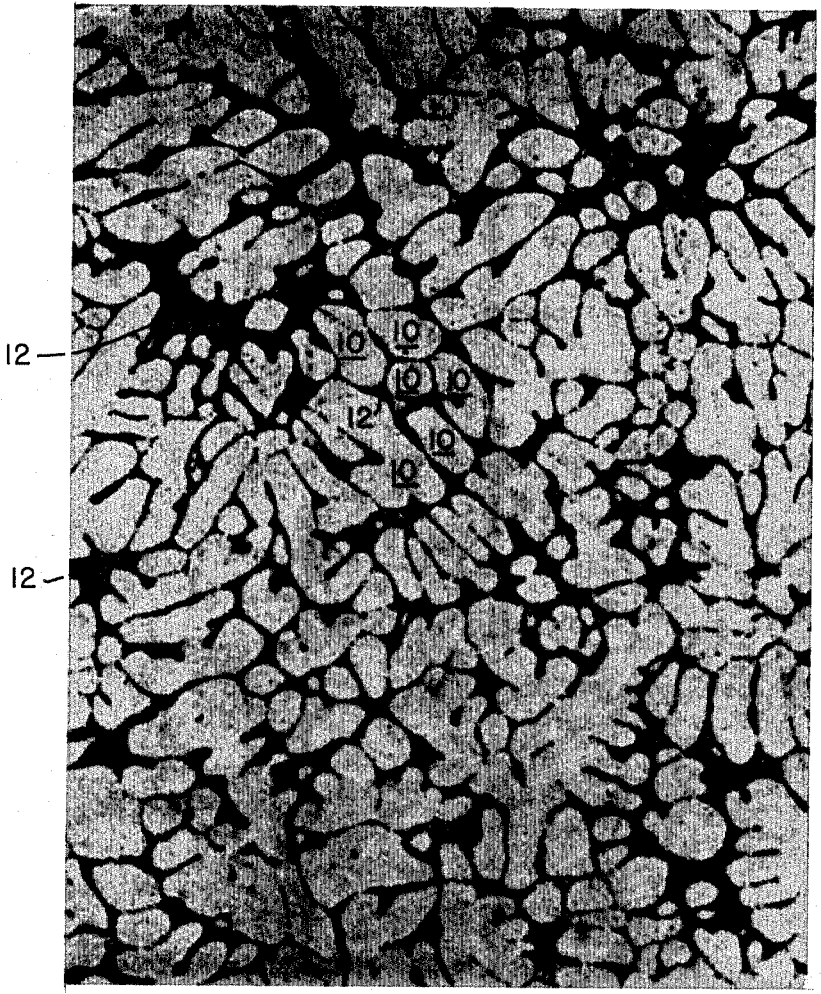
FIGS. 1A and 1B are photomicrographs (magnified 100×) of the as-cast and heat treated conditions of a cast aluminum alloy based sample.
Figure 1B:
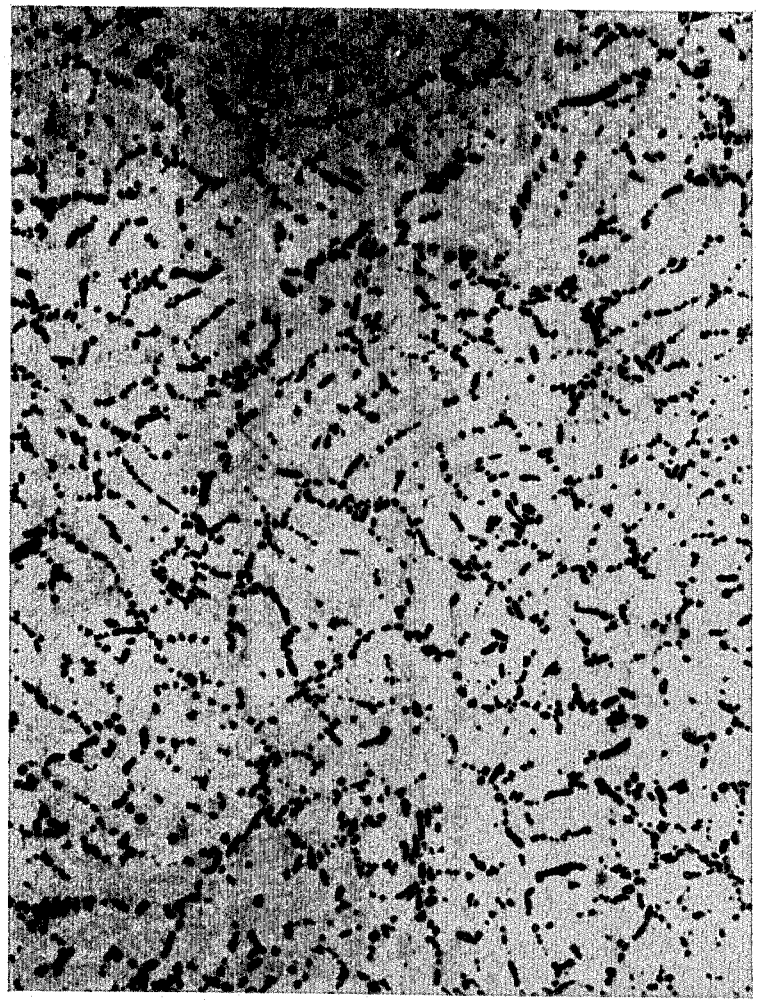
Figure 1C:
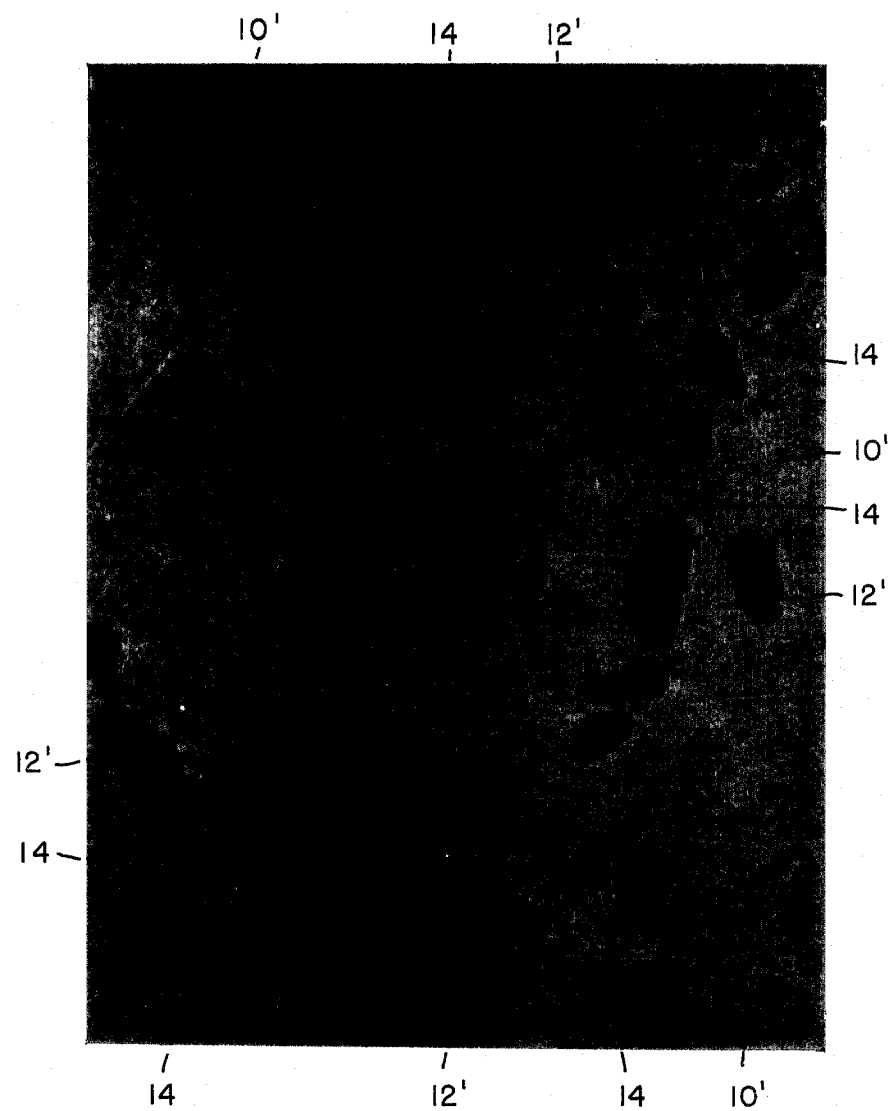
FIG. 1C is an enlarged portion of a heat treated portion of FIG. 1A (magnified 1200×).

FIG. 1A is a photomicrograph magnified 100× of the surface of a selected zone of a casting (as-cast) of an aluminum based alloy known in the art as an A357 alloy. FIG. 1B is a photomicrograph of the surface of the casting zone of FIG. 1A after solution heat treatment to a −T6 condition per MIL-H-6088, i.e., solution treated at 1005° F. for 18 hours; 140° F. water quench; 20 hours natural age followed by 10 hours at 325° F. artificial age. FIG. 1C is a photomicrograph of the surface of the −T6 heat treated casting zone of FIG. 1A magnified 1200 times.

Referring now to FIGS. 1A, 1B and 1C, the major difference observed throughout these views is the appearance of silicon which forms cell boundaries. In the as-cast condition of FIG. 1A, light colored aluminum cells 10 are completely surrounded by dark colored silicon 12 forming long, needle-like slivers. Solution heat treatment (see FIG. 1B) transforms the silicon into rounded individual particles 12′ with no apparent affect on the size or shape of the aluminum cells 10′. In the heat treated condition illustrated in FIG. 1B, cell boundaries are less definite but are still outlined generally by silicon particles 12′ (seen more clearly in FIG. 1C).

The ductility measurement of a volume of a zone of a cellular metallic such as the A357 alloy can be nondestructively ascertained in the present invention by first preparing an exposed surface area of the zone of the casting to be measured. After surface preparation, the number of metal cells in that surface area is counted either manually or using an automated image analysis technique. The cell count may then be directly correlated to total elongation (ductility) of the zone using the following general relationship:

$$EL = e^{\{\frac{AN^B - C}{D}\}}$$

Where
EL = total elongation (ductility) in percent
N = cells counted per unit area, e.g., 0.0001 sq. in.
A, B, C, D = empirical constants.

The above elongation-cell count relationship has been developed as follows:

Tensile coupon test results and cell count measurements must be obtained from a sufficient quantity of casting zones to properly describe the mechanical behavior of the casting. The difference between tensile ultimate strength (TUS) and tensile yield strength (TYS) may be defined as the excess stress ($\Delta$) of that zone, i.e., $$\Delta = TUS - TYS$$

When the ductility in a zone is small, excess stress will not be very large. When excess stress is zero, ductility, or elongation is, by definition, 0.2 percent. A mechanical equation of state of the following form should be developed between excess stress and elongation with the tensile data obtained as above:

$$\Delta = D\, \mathrm{Log}_e EL + C$$

The empirically derived constants (C,D) should be established statistically to satisfy the boundary condition of $\Delta = 0$ when EL = 0.2, as will be shown. Cell count measurements (N) from the same tensile tested casting zones form a simple power function with excess stress.

$$\Delta = A(N)^B$$

The empirical constants (A,B) are determined by regression of excess stress on cell counts using this power function, least squares, best fit model. The naturally greater difficulty in measuring tensile elongation, coupled with small amounts of test data, requires that excess stress be related to cell counts. The mechanical equation of state previously established can then be utilized to relate cell counts to elongation.

$$\Delta = D\mathrm{Log}_e EL + C = A(N)^B$$

or $$EL = e^{\{\frac{AN^B - C}{D}\}}$$

A statistical analysis may be used to determine the empirical constants as follows:

$$\Delta = D\, \mathrm{Log}_e EL + C \qquad 1.$$

excess stress values: $\Delta_1, \Delta_2, \Delta_3 \ldots \Delta_n$
elongation values: $EL_1, EL_2, EL_3 \ldots El_n$
Determine slope (D) of each ($\Delta_i$, $EL_i$) coordinate $$D_i = \frac{\Delta_i - 0}{\mathrm{Log}_e EL_i - \mathrm{Log}_e 0.2}$$

Average Slope:

$$D = \frac{\sum_{i=1}^{n} D_i}{n}$$

Since $\Delta = 0$ at EL = 0.2, $C = D\, \mathrm{Log}_e 0.2 = 1.609D$ $$\Delta = AN^B \qquad 2.$$

excess stress values: $\Delta_1, \Delta_2, \Delta_3 \ldots \Delta_n$
cell count values: $N_1, N_2, N_3 \ldots N_n$
By regression of ($\Delta$) on (N):

$$B =$$

-continued $$\frac{\sum_{i=1}^{n} (Log_e N_i)(Log_e \Delta_i) - \frac{\left(\sum_{i=1}^{n} Log_e N_i\right)\left(\sum_{i=1}^{n} Log_e \Delta_i\right)}{n}}{\sum_{i=1}^{n} (Log_e N_i)^2 - \left(\sum_{i=1}^{n} Log_e N_i\right)^2 / n}$$

and $$A = exp^a$$

where $$a = \frac{\sum_{i=1}^{n} Log_e \Delta_i}{n} - \frac{B \sum_{i=1}^{n} Log_e N_i}{n}$$

For an A357-T6 casting the empirical constants are:
A=1.5
B=0.543
C=4.81
D=2.86

It will be understood that these constants will be different for other cellular metallics.

Since the relationship between elongation and cell counts is developed empirically from tensile test data it should be vertified for all castings during preproduction as both chemistry and heat treatment influence elongation with little effect on the cellular structure. Finally, one must account for cell count gradients through the thickness of the casting for appreciable casting thickness due to different rates of solidification.

Counting cells raises the question of the definition of a cell. Cell definition includes two considerations. First, in the −T6 condition illustrated in FIGS. 1B and 1C, many small light colored aluminum cellular zones 14 (see FIG. 1C) less than 10 micrometers in dimension can be observed among silicon particles. These zones 14 may be disregarded when making cell counts according to the present invention since they are substantially non-contributive to ductility limitations, as will be understood. Second, the incomplete outlining of larger aluminum cells by silicon particles causes a degree of subjectivity requiring human judgement in ascertaining whether such cells are one or more cells.

Figure 2:
FIG. 2 is a block diagram of an image analysis system useful for automatically counting the cells of a cellular metallic sample according to the present invention.

The former consideration is facilitated and the latter consideration is eliminated by using an automated image analysis machine for metal cell counts (see FIG. 2). As shown in FIG. 2, after the surface of a particular zone of the casting sample is prepared, in a manner discussed hereinafter, a conventional television camera having appropriate conventional optics may be focused upon the microstructure of the zonal surface in which cells are to be counted. The camera transmits its image signal to a conventional analog digital converter. The converter provides a computer with information representative of the image focused upon by the television camera whereby the microstructural image may be displayed in a conventional manner on a television display.

In use of the image analysis machine of FIG. 2, different brightnesses of the image are transformed into electrical signals by the analog digital converter for quantitative processing. All aluminum cells appear as one gray scale value. Silicon and pores in the cellular metallic appear as two other gray scale values. An image of the viewed microstructure zone can therefore be partitioned for operation on any constituent, i.e., aluminum cells, silicon, or pores.

In the case of aluminum cells, very small zones of aluminum existing between silicon particles can be eliminated when counting cells (since substantially noncontributive to ductility limitations) by utilizing the logic capability of the computer illustrated in FIG. 2. A process known in the trade as erosion may be used to remove excessive outer layers of all aluminum elements in the two dimensional image transmitted by the television camera. This permits the smallest aluminum zones to vanish whereby dilation of the image to its original state enlarges only those zones which have not vanished. The reconstructed image can then be eroded until all aluminum zones vanish. The number of erosion steps required for each aluminum zone to disappear is equivalent to the size of such zones. During this process of image erosion, narrowly connected zones of aluminum will become separated into two or more discrete elements. This is seen most clearly in FIG. 1C. Each element will be counted as an individual cell.

As discussed above small non-contributing aluminum zones are eliminated from the counts and all remaining zones become partitioned automatically into cells of various sizes. The non-contributing cells must be ascertained by trial and error wherein nondestructive tests according to the present invention are compared with destructive tensile tests of tensile coupons. In general, it has been found that metal cells much smaller than the average metal cell size may be ignored. Only in this manner may the system of FIG. 2 be programmed to ignore cells which do not contribute substantially to ductility limitations.

As a result of using this automated technique the subjectivities associated with manual cell counting may be substantially eliminated. The image may also be displayed on a video screen to allow an operator to selectively focus, position the specimen and measure constituents of interest. In actual use, the main interest was devoted to cast aluminum cells including primary and secondary dendrite arms as well as those resulting from coarsening and multiplication.

Figure 3:
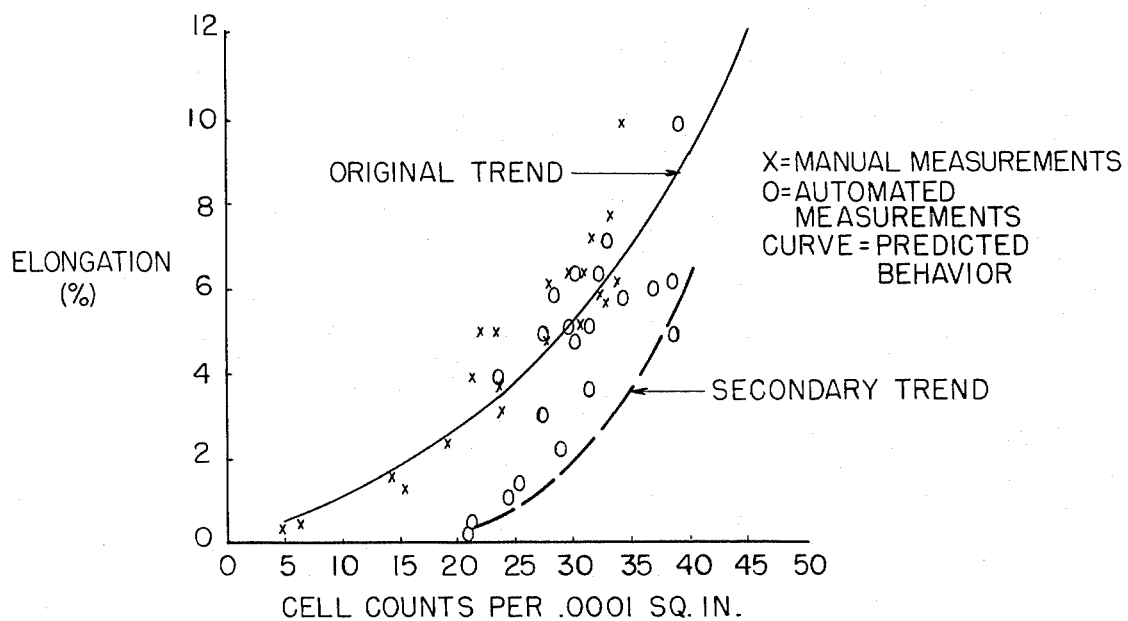
FIG. 3 represents manual and machine cell count measurements plotted against elongation data obtained from full range stress-strain curves.

Typical results from manual and automated examinations are shown in FIG. 3. Two sets of symbols are shown in FIG. 3 representing the manual (X) and the machine (O) cell counting measurements plotted against elongation data obtained from full-range stress-strain curves. As can be clearly seen, automated cell counts form a coherent trend compared to manual cell counts indicating loss of subjectivity. An original trend and a secondary trend curve have been given for a purpose to be explained hereinafter.

Measurements using the automated image analysis system of FIG. 2 are not only less subjective and faster then those obtained manually but allow the scanning of much larger areas. All of the machine measured cell counts in FIG. 3 were made from 15 fields scans of the surface area of the selected zone in which each field was approximately 0.0005 square inches. Clearly, an automated image analysis system is more accurate and suffers less from scattering than manual results. A suitable image analysis system has been found to be the Texture Analysis System (TAS) sold by Leitz Company, Rockleigh, N.J. 07647. The programming of this system must be modified in accordance with the above principles in order to perform the process of the present invention.

It should be noted that cell counts are based on a unit surface area. The unit area utilizable in the present invention may be a projected planar area. This means that the television camera of the image analysis system need not be precisely oriented relative to the selected zone sought to be measured of the casting sample. The television camera merely sights upon the surface area of the zone in question after surface preparation whereby the cells may be quickly counted by the automated image analysis system. Clearly, manual counts may also be made using a projected planar area.

As was alluded to above, the surface of the casting zone to be measured should be metallographically prepared prior to the counting of the cells in that zone. It is important that the surface be prepared to maximize the possibility that the TAS or the person making manual cell counts can readily define a cell, i.e., surface preparation facilitates cell appearance definition. While other procedures may exist, a suitable procedure for surface preparation has been found to comprise the following steps.

The surface is first ground and polished using a conventional flexible-shaft power tool having a high speed and a low speed range. Rubberized abrasive wheels and the high speed range of the power tool should be used for grinding an area approximately one half inch square. Light pressure ensures an even finish and long wheel life. Successively finer grinds should cover a slightly smaller area with the final area being about one quarter of an inch in diameter. In practice, best results have been achieved using theee grinding steps: a rough grind with a course wheel (approximately 100 grit), an intermediate grind with a fine wheel (approximately 240 grit), and a fine grind with an extra fine wheel (approximately 400 grit). Each successive grinding operation should be done at 90° to the previous grind whereby the formation of grooves on the surface may be minimized. Practice has shown that about 30 to 60 seconds of grinding are required.

The slow speed range of the power tool may be used for the polishing process. Polishing may be effected with a cotton swab attached to a wooden stick after any grinding residue is removed using acetone (or any clear solvent) and cotton. The stick of the cotton swab may be secured within the chuck of the power tool and checked to ensure a reasonably true spin. A small amount of a 6-micron diamond paste may be applied to the cotton swab tip coupled with one or two drops of kerosene for lubrication.

In use, the swab is spun and gently applied to the previously ground area in a smooth circular path. Preferably, the zone to be measured is again cleaned with cotton and acetone and the polishing procedure repeated using a 1-micron diamond paste.

After grinding and polishing the surface is chemically etched for 30 to 60 seconds using a primary etchant. In the case of an A357-T6 aluminum alloy, a suitable primary etchant has been found to be a reagent consisting of a solution of 1% hydroflouric acid (HF), 1.5% hydrochloric acid (HCl) and 2.5% nitric acid (HNO$_3$) in water. An alternative primary etchant is a 0.5 percent hydrofluoric acid solution etchant.

The above etching step presumes that the surface polished to be observed is horizontal. If the polished zone is not horizontal it may be etched using a saturated cotton swab. Normal etching time has been found to be one-half to one minute.

Specimen configuration, the presence of pores or voids which act as stress risers or strain concentrations and eutectic morphology, i.e., in the case of the A357-T6 alloy the size and shape of silicon particles forming cell boundaries, modify the predicted ductility calculated from unit area cell counts.

Figure 4:
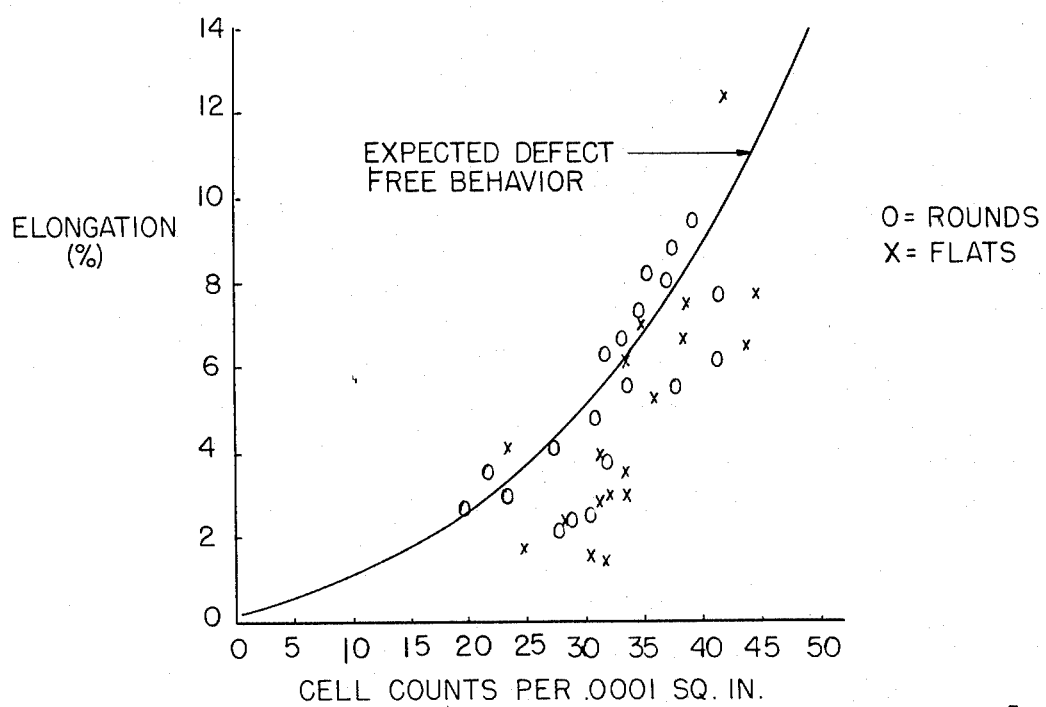
FIG. 4 is a graph illustrating the effect of the sample structural configuration upon test results derivable from the automated image analysis system illustrated in FIG. 2.

FIG. 4 illustrates the effect of specimen configuration upon the test method of the present invention as it applies to the A357-T6 casting. As can be seen, an automated examination provides data showing a difference between round (O) and flat (X) specimen ductilities when compared to the expected defect free behavior curve. With the same number of aluminum cells counted in a unit projected area, flat specimen ductilities were less than dustilities from round specimens of the same casting. While the specimen configuration effects on ductility are not completely understood it is believed that unless the specimen thickness approaches the width one cannot expect an accurate measure of casting ductility using the present invention. A thickness of width ratio of 0.8 or greater has been found useful. Machining surfaces and rounding corners of flat specimens may minimize configuration effects, however. Finally, surface finish and sharpness of corners of the specimen structure may have an influence upon the accuracy of the present invention but this is not fully understood.

Figure 5:
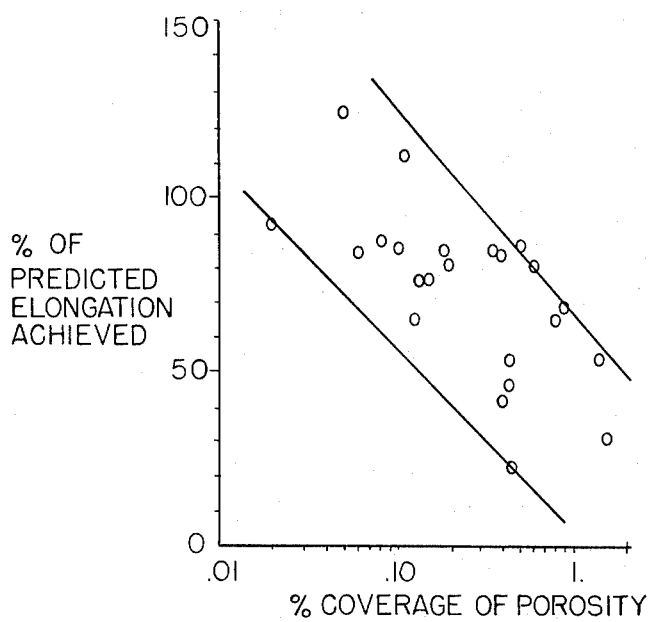
FIG. 5 is a graph illustrating the effect of porosity on predicted ductility.

Porosity also has an effect upon the cell count-elongation relationship. FIG. 5 illustrates the trend of the effect of porosity upon the basic relationship of the present invention for an A357-T6 alloy casting. The ordinate is the percentage of predicted elongation actually achieved in destructive tensile tests. The two lines define the boundary of the data indicating the trend of the effect of porosity. FIG. 5 ignores the effect of silicon particle size and clearly shows that as the percentage of porosity in the observed cellular matrix increases, deviations between the measured and predicted values of ductility also increase. Calibration efforts have shown that multiple field scans are required to obtain accurate porosity measurements. The present invention is consequently inapplicable to castings which contain gross defects such as gas holes, cold shuts, cracks, etc. It is applicable, however, to gaseous and shrinkage porosities evenly distributed and identifiable according to ASTM E155 soundness grades A, B and C.

Figure 6:
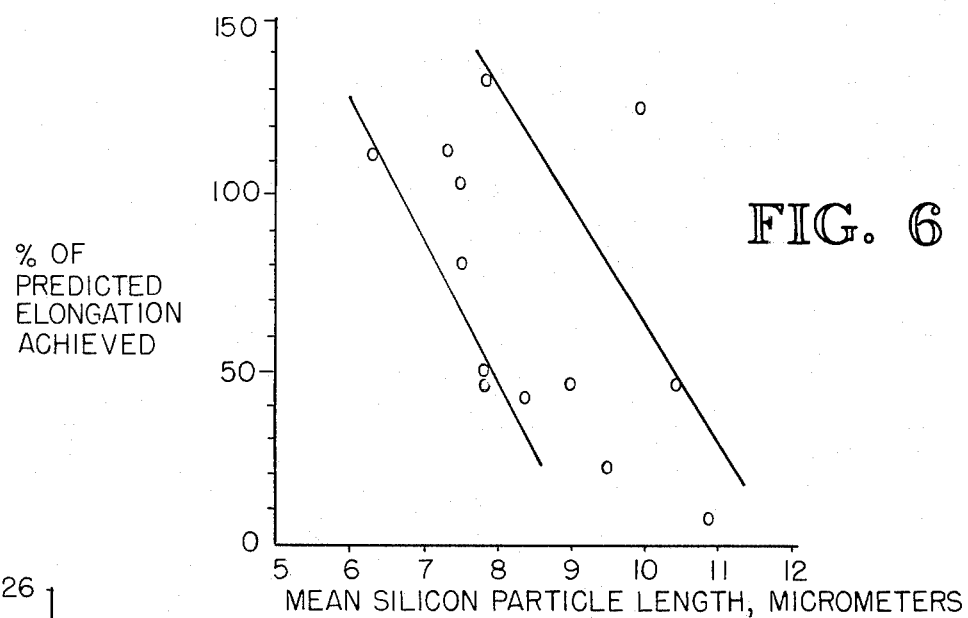
FIG. 6 is a graph illustrating the effect on predicted elongation due to silicon particle size.

Eutectic morphology or cell boundary element size, i.e., the silicon particle size is also a factor to be taken into account when applying the nondestructive testing method of the present invention to a cast A357-T6 aluminum alloy. In FIG. 6, the effect of porosity is unaccounted for whereby a rough estimate (shown between the two lines) of the effect of silicon particle size upon the predicted elongation achieved through destructive testing is ascertained. The percentage of predicted elongation achieved is used as the independent variable. Measurements of 1000 to 2000 silicon particles per specimen (five fields were measured) were used to compute mean particle lengths and are shown as abscissa values. As can be seen, ductility prediction is improved for small particle sizes. The spread among results is sizable indicating a need for improvement in the understanding of the effect of the parameter. Finally, it should be noted that influences on ductility due to chemistry have not been partitioned in either FIG. 5 or FIG. 6.

Figure 7:
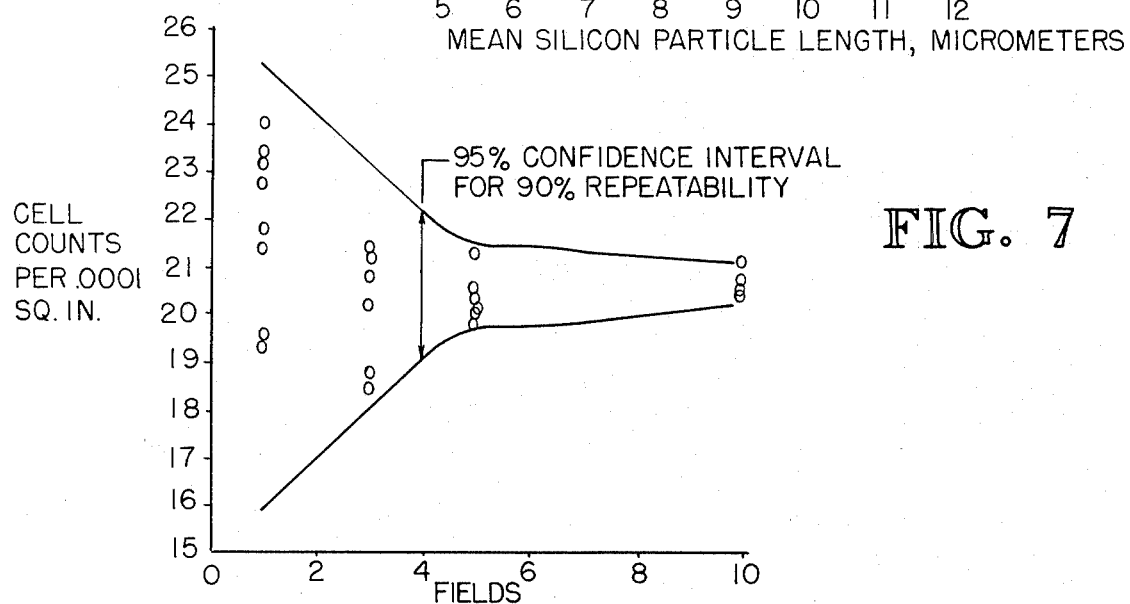
FIG. 7 is a graph illustrating a cell count measurement calibration.

Calibration of the TAS showed that a scan between five and ten fields would provide 90% or more repeatability (see FIG. 7). Repetitive measurements for the number of cells were made using one, three, five and ten fields to develop the convergence shown between the two lines in FIG. 7. As expected, scatter among repetitive measurements decreases as the number of fields scanned is increased. Assuming that the TAS cell count measurements in FIG. 3 are accurate it is clear that there exists more than one unique cell count-elongation relationship shown as the solid curve and designated the original trend. Most likely there are a family of unique curves, one of which is shown as the dashed curve (designated secondary trend) representing higher porosity, less modified silicon or concentrations of those chemical elements deleterious to ductility.

The above method should be applicable to any cellular metallic. While the effects of the parameters of sample structural configuration, porosity and cell boundary element size (eutectic morphology) have been discussed with respect to a casting made of A357-T6 aluminum cellular metallic, the trends are identical for other cellular metallics. These parameters may have different relative effects on other cellular metallics but the trends will be as discussed earlier.

Obviously many variations of the present invention are possible in light of the above teachings. It is therefore to be understood that within the scope of the appended claims the invention may be practiced otherwise than as specifically described.

What is claimed and desired to be secured by Letters Patent of the United States is:

1. A method for nondestructively measuring the ductility of a cellular metallic, comprising:
   providing a cellular metallic,
   selecting an arbitrary zone of said metallic wherein a measurement is to be made,
   counting substantially all of the metal cells within a surface area of said zone, and
   correlating the number of said metal cells per unit area to the ductility of said zone of said cellular metallic.

2. The method of claim 1, wherein the number of cells is correlated to the ductility of said cellular metallic according to the following relationship:

$$EL = e^{\{\frac{ANB-C}{D}\}}$$

where
   EL = total average elongation (ductility) in percent
   N = number of metal cells per unit area
   A, B, C, D, = empirical constants.

3. The method of claims 1 or 2, wherein the number of metal cells per unit area which do not significantly contribute to the ductility of said zone of said cellular metallic are not counted.

4. The method of claim 3, wherein said surface area is a projected area.

5. The method of claim 4, wherein said surface area is polished and chemically etched prior to counting said metal cells.

6. A method for nondestructively measuring the ductility of a cellular metallic, comprising:
   providing a cellular metallic,
   selecting a zone of said metallic wherein a measurement is to be made,
   counting substantially all of the metal cells within a surface area of said zone, and
   correlating the number of said metal cells per unit area to the ductility of said zone of said cellular metallic according to the following relationship:

$$EL = e^{\{\frac{ANB-C}{D}\}}$$

where
   EL = total average elongation (ductility) in percent.
   N = number of metal cells per unit area
   A, B, C, D, = empirical constants.

7. The method of claim 6, wherein the number of metal cells per unit area which do not significantly contribute to the ductility of said zone of said cellular metallic are not counted.

8. The method of claim 7, wherein said surface area is a projected area.

9. The method of claim 8, wherein said surface area is polished and chemically etched prior to counting said metal cells.

* * * * *